United States Patent [19]

Cantatore et al.

[11] Patent Number: 4,859,724
[45] Date of Patent: Aug. 22, 1989

[54] BICYCLIC PIPERIDINE COMPOUNDS FOR USE AS STABILIZERS FOR ORGANIC MATERIALS

[75] Inventors: Giuseppe Cantatore, Bitonto; Valerio Borzatta, Bologna, both of Italy

[73] Assignee: Ciba-Geigy Corporation, Ardsley, N.Y.

[21] Appl. No.: 198,269

[22] Filed: May 25, 1988

[30] Foreign Application Priority Data

Jun. 2, 1987 [IT] Italy ............................. 20750 A/87

[51] Int. Cl.$^4$ ............................................. C08K 5/34
[52] U.S. Cl. ..................................... 524/91; 544/350; 252/403
[58] Field of Search .......................... 524/91; 544/350; 252/403

[56] References Cited

U.S. PATENT DOCUMENTS 3,736,321  5/1973  Mee et al. ......................... 544/350
4,238,388  12/1980  Cantatore et al. .................. 524/98
4,279,804  7/1981  Cantatore et al. .................. 524/95

Primary Examiner—John Kight
Assistant Examiner—Kriellion Morgan
Attorney, Agent, or Firm—Harry Falber

[57] ABSTRACT

Bicyclic piperidine compounds of the general formula (I)

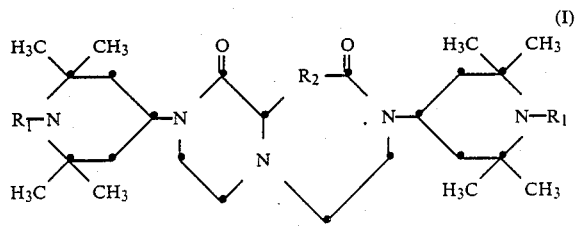

in which $R_1$ is hydrogen, O•, OH, NO, $CH_2CN$, $C_1$-$C_8$-alkyl, allyl, benzyl, $C_1$-$C_8$-acyl, OH-monosubstituted $C_2$-$C_4$-alkyl, 2,3-epoxypropyl, $C_1$-$C_{18}$-alkyloxy, $C_5$-$C_{12}$-cycloalkyloxy or 2,3-dihydroxypropyl and $R_2$ is a direct bond or —$CH_2$—, can be used as light stabilizers, heat stabilizers and oxidation stabilizers for organic materials, in particular, synthetic polymers.

12 Claims, No Drawings

BICYCLIC PIPERIDINE COMPOUNDS FOR USE AS STABILIZERS FOR ORGANIC MATERIALS

The present invention relates to novel bicyclic piperidine compounds, the use thereof as light stabilizers, heat stabilizers and oxidation stabilizers as well as to the stabilized organic materials.

It is known that synthetic polymers undergo progressive changes in their physical properties, such as loss of mechanical strength and colour changes, when they are exposed to sunlight or other sources of ultraviolet light in the presence of oxygen.

To retard the deleterious effect of ultraviolet radiation on synthetic polymers, it has been proposed to use various additives having light-stabilizing properties, e.g. those described in U.S. Pat. Nos. 4,238,388 and 4,279,804.

The present invention relates to novel piperidine compounds of the general formula (I)

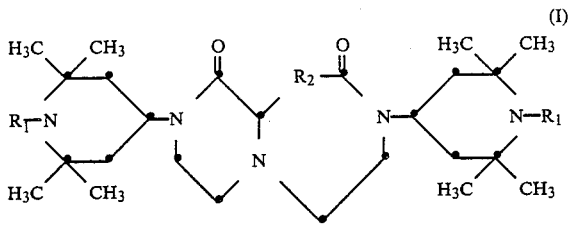

in which $R_1$ is hydrogen, O·, OH, NO, $CH_2CN$, $C_1$–$C_8$-alkyl, allyl, benzyl, $C_1$–$C_8$-acyl, OH-monosubstituted $C_2$–$C_4$-alkyl, 2,3-epoxypropyl, $C_1$–$C_{18}$-alkyloxy, $C_5$–$C_{12}$-cycloalkyloxy or 2,3-dihydroxypropyl and $R_2$ is a direct bond or —$CH_2$—.

Representative examples of $R_1$ as $C_1$–$C_8$-alkyl are methyl, ethyl, propyl, butyl, isobutyl, pentyl, hexyl, heptyl and octyl. $C_1$–$C_4$-alkyl, in particular methyl, is preferred.

$R_1$ as $C_1$–$C_8$-acyl may be an aliphatic or aromatic acyl group. $C_1$–$C_8$-alkanoyl, $C_3$–$C_8$-alkenoyl and benzoyl are preferred. Examples are formyl, acetyl, propionyl, butyryl, valeryl, hexanoyl, octanoyl, benzoyl, acryloyl and crotonoyl. Acetyl is preferred.

Representative examples of $R_1$ as $C_2$–$C_4$-alkyl monosubstituted by OH, preferably in the 2, 3 or 4 position, are 2-hydroxyethyl, 2-hydroxypropyl, 3-hydroxypropyl, 2-hydroxybutyl and 4-hydroxybutyl. 2-Hydroxyethyl is preferred.

$R_1$ as $C_1$–$C_{18}$-alkyloxy is for example methoxy, ethoxy, n-propoxy, n-butoxy, sec-butoxy, tert-butoxy, n-hexyloxy, n-octyloxy, 2-ethylhexyloxy, n-nonyloxy, n-decyloxy, n-undecyloxy, n-dodecyloxy, n-tridecyloxy, n-tetradecyloxy, n-hexadecyloxy or n-octadecyloxy. $C_6$–$C_{12}$-alkyloxy, in particular heptyloxy and octyloxy, is preferred.

$R_1$ as $C_5$–$C_{12}$-cycloalkyloxy is for example cyclopentyloxy, cyclohexyloxy, cyclooctylosy, cyclononyloxy or cyclododecyloxy. Cyclopentyloxy and cyclohexyloxy are preferred.

Those compounds of the formula (I) are preferred, in which $R_1$ is hydrogen, $CH_2CN$, $C_1$–$C_4$-alkyl, allyl, benzyl, acetyl or OH-monosubstituted $C_2$–$C_3$-alkyl.

Those compounds of the formula (I) are particularly preferred, in which $R_1$ is hydrogen, methyl, allyl or acetyl.

Those compounds of the formula (I) are of special interest, in which $R_1$ is hydrogen, methyl, allyl or acetyl and $R_2$ is —$CH_2$—.

Those compounds of the formula (I) are of particular interest, in which $R_1$ is hydrogen or methyl and $R_2$ is —$CH_2$—.

The compounds of the formula (I) can be prepared by analogy to known processes.

If $R_2$ is a direct bond and $R_1$ is H, the compounds of the formula (I) can be prepared, for example, according to Scheme 1, by reacting a compound of the formula (II) with a halogenomalonate of the formula (III), in which $R_4$ is preferably methyl or ethyl and X is preferably chlorine or bromine.

SCHEME 1:

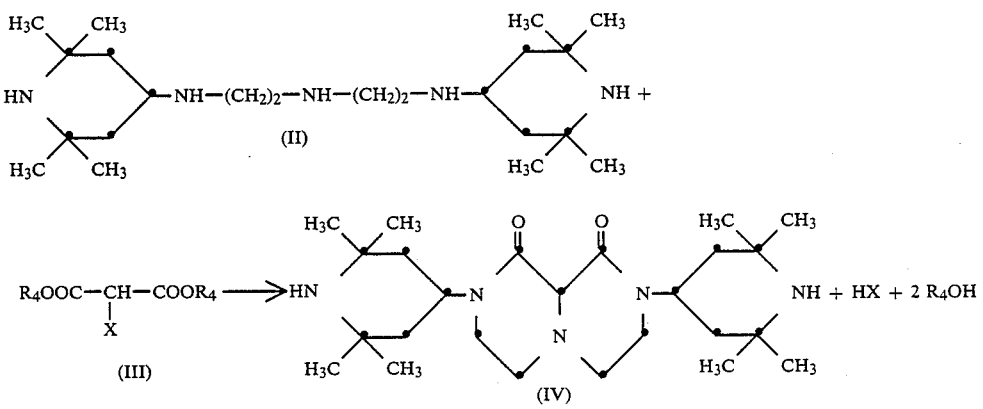

If $R_2$ is —$CH_2$— and $R_1$ is H, the compounds of the formula (I) can be prepared, for example, according to Scheme 2, by reacting a compound of the formula (II) with dimethyl or diethyl esters of maleic or fumaric acid.

SCHEME 2:

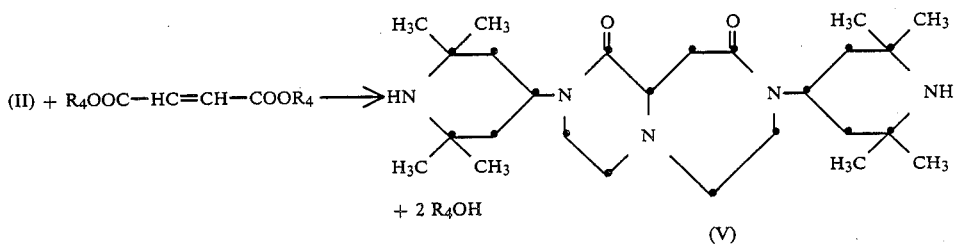

(II) + R$_4$OOC—HC=CH—COOR$_4$ ⟶ (V) + 2 R$_4$OH

The corresponding compounds substituted on the piperidine N are conveniently prepared from the compounds of the formula (IV) or (V) by means of the conventional processes of the state of the art.

The reactions are preferably carried out in inert solvents, for example in toluene, oxylene, ethylbenzene, trimethylbenzene, decalin, dibutyl ether, 1,2-dimethoxyethane, 1,2-diethoxyethane, diethylene glycol dimethyl ether, diethylene glycol diethyl ether, N,N-dimethylformamide, N,N-dimethylacetamide, N-methylpyrrolidone or dimethyl sulfoxide.

In the case of the reaction according to Scheme 1, an inorganic base, for example sodium or potassium hydroxide or carbonate, is conveniently used for neutralizing the hydrogen halide acid liberated.

The compound of the formula (II), which can be used for preparing the compounds according to the present invention, is obtained by known processes, for example as described in EP-A-61,785, by reductive alkylation of diethylenetriamine with 2,2,6,6-tetramethyl-4-piperidone in the presence of hydrogenation catalysts such as e.g. platinum and palladium.

As mentioned at the outset, the compounds of the formula (I) are very effective in improving the light stability, heat stability and oxidation stability of organic materials, in particular synthetic polymers and copolymers.

Therefore, a further object of the invention is a composition comprising an organic material subject to thermal, oxidative or light-induced degradation and at least one compond of the formula (I).

Examples of organic materials which can be stabilized are:

1. Polymers of monoolefins and diolefins, for example, polypropylene, polyisobutylene, polybutene-1, polymethylpentene-1, polyisoprene or polybutadiene, as well as polymers of cycloolefins, for instance of cyclopentene or norbornene, polyethylene (which optioanlly can be crosslinked), for example high density polyethylene (HDPE), low density polyethylene (LDPE) and linear low density polyethylene (LLDPE).

2. Mixtures of the polymers mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example C$_5$–C$_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/-butadiene/ethyl acrylate, styrene/acrylonitrile/methyl acrylate; mixtures of high impact strength from styrene copolymers and another polymer, such as, for example, from a polyacrylate, a diene polymer or an ethylene/-propylene/diene terpolymer; and block copolymers of styrene, such as, for example, styrene/butadiene/styrene, styrene/isoprene/styrene, styrene/ethylene/-butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl bonzoate, polyvinyl maleate, polyvinyl butyral, polyallyl phthalate or polyallylmelamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxy groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepred from hexamethylenediamine and isophthalic or/and terephthalic acid and optionally an elastomer as modifer, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane]terephthalate and polyhydroxybenzoates as well as block-copolyetheresters derived from polyethers having hydroxy end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents. 25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be mixed with the material to be stabilized in various proportions depending on the nature of the polymer, the end use and the presence of other additives.

In general, it is appropriate to use 0.01 to 5% by weight of the compounds of the formula (I), relative to the weight of the polymers, preferably from 0.05 to 1%. The compounds of the formula (I) can be incorporated into the polymeric materials by various processes, such as dry blending in the form of powders, or wet mixing in the form of solutions or suspensions or also in the form of a masterbatch; in these operations, the polymer can be employed in the form of powder, granules, solutions, suspensions or in the form of a latex.

The polymer compositions stabilized with the products of the formula (I) can be used for the preparation of moulded articles, films, tapes, monofilaments, surface-coatings and the like.

If desired, other additives, such as antioxidants, UV absorbers, nickel stabilizers, pigments, fillers, plasticizers, antistatic agents, flame-proofing agents, lubricants, corrosion inhibitors and metal deactivators, can be added to the compositions comprising the compounds of the formula (I) and the synthetic polymers.

Examples of additives which can be mixed with the compounds of the formula (I) are in particular:

1. Antioxidants 1.1. Alkylated monophenols, for example 2,6-di-tert-butyl-4-methyl-phenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-iso-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol, 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

1.5. Benzyl compounds, for example 1,3,5-tris(3,5-di-tert-butyl-4-hydroxybenzyl)-2,4,6-trimethylbenzene, bis (3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5-dicyclohexyl-4-hydroxybenzyl)isocyanurate.

1.6. Acylaminophenols, for example 4-hydroxyanilide of lauric acid, 4-hydroxyanilide of stearic acid, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl) oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3', 5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4- butanetetracarboxylate, 1,1'-(1,2-ethanediyl)bis-(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis(2,4-di-tert-butylphenyl) 4,4'-biphenylene diphosphonite, 3,9-bis-(2,4-di-tert-butylphenoxy)-2,4,8,10-tetraoxa-3,9-diphosphaspiro[5.5]-undecane.

5. Peroxide scavengers, for example esters of $\beta$-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis($\beta$-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

EXAMPLE 1

A mixture of 152.66 g (0.4 mol) of N,N'-bis-(2,2,6,6-tetramethyl-4-piperidyl)-diethylenetriamine, 57.65 g (0.4 mol) of dimethyl fumarate and 150 ml of trimethylbenzene is heated for 4 hours under reflux with removal of the methanol liberated during the reaction. After cooling to 40° C., 220 ml of acetone are added.

The resulting precipitate is separated off by filtration, washed with 150 ml of acetone and dried at 130° C. in vacuo (24 mbar). This gives the compound of the formula

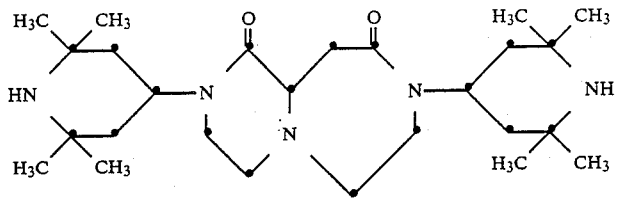

of melting point 324°–325° C.

Analysis for $C_{26}H_{47}N_5O_2$: Calculated: C=67.64%; H=10.26%; N=15.17% Found: C=67.59%; H=10.27%; N=15.12%

EXAMPLE 2

21.10 g of dimethyl bromomalonate are added slowly at room temperature to a solution of 38.16 g (0.1 mol) of N,N'-bis-(2,2,6,6-tetramethyl-4-piperidyl)-diethylenetriamine in 150 ml of dichloromethane. The mixture is left to stand for 1 hour at room temperature, then cooled to 0° C. and treated with a solution of 4.40 g (0.11 mole) of sodium hydroxide in 30 ml of water, the temperature being maintained at 0°–5° C. The aqueous phase is separated off and 200 ml of xylene are added to the organic phase.

The resulting solution is slowly heated, with removal of the dichloromethane, the residual water and the methanol liberated during the reaction, until the reflux temperature is reached, which is maintained for 10 hours.

After cooling to room temperature, the precipitate which has formed is separated off by filtration and dried at 140° C. in vacuo (24 mbar).

This gives the compound of the formula

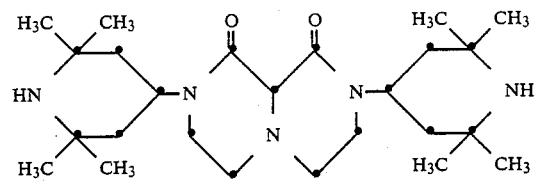

of melting point 200°–222° C.

Analysis for $C_{25}H_{45}N_5O_2$: Calculated: C=67.08%; H=10.13%; N=15.64% Found: C=66.92%; N=10.02%; N=15.56%

EXAMPLE 3

23.08 g (0.05 mol) of the compound prepared in Example 1 is added in portions to a soluton of 9.21 g (0.2 mol) of formic acid in 50 ml of water.

6 g (0.2 mol) of paraformaldehyde are added to the solution thus obtained, and the mixture is then heated under reflux for 10 hours. After cooling to 10°–15° C., a solution of 12 g (0.3 mol) of sodium hydroxide in 40 ml of water is added slowly, while maintaining the above temperature. The resulting precipitate is separated off by filtration, washed with water, dried and crystallized from a 1/1 volume mixture of ethanol and isopropanol.

This gives the compound of the formula

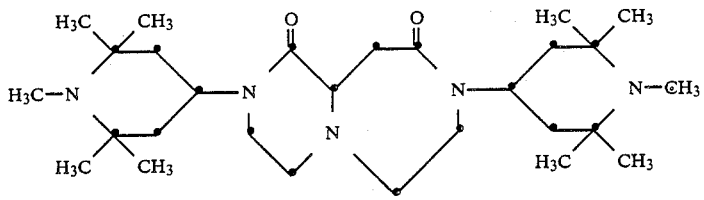

of melting point 314°–315° C.

Analysis for $C_{28}H_{51}N_5O_2$: Calculated: C=68.67%; H=10.50%; N=14.30% Found: C=68.40%; H=10.46%; N=14.18%

EXAMPLE 4

A mixture of 23.08 g (0.05 mol) of the compound prepared in Example 1, 18.15 g (0.15 mol) of allyl bromide, 22.11 g (0.16 mol) of anhydrous, finely ground potassium carbonate, 1.66 g (0.01 mol) of potassium iodide and 150 ml of 2-butanone is heated under reflux for 24 hours.

After cooling, the reaction mixture is filtered and evaporated in vacuo (24 mbar). The residue is taken up in 120 ml of dichloromethane, and the solution is washed twice with water, dried over anhydrous sodium sulfate and evaporated.

The resulting residue is crystallized from methanol.

This gives the compound of the formula

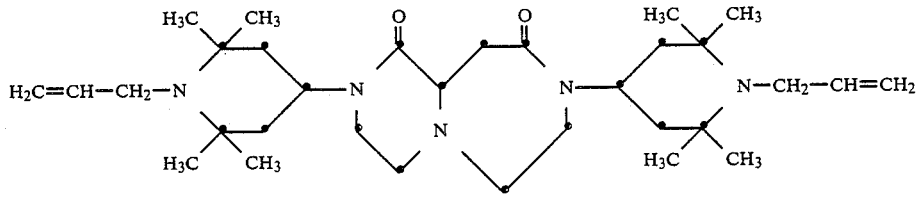

of melting point 271°–273° C.

Analysis for $C_{32}H_{55}N_5O_2$: Calculated: C=70.94%; H=10.23%; N=12.93% Found: C=70.96%; N=10.21%; N=12.78%

EXAMPLE 5

A mixture of 23.08 g (0.05 mol) of the compound prepared in Example 1, 51.04 g (0.5 mol) of acetic anhydride and 150 ml of pyridine are heated under reflux for 4 hours.

After cooling to room temperature, the precipitate thus obtained is separated off by filtration, washed with acetonitrile and dried in vacuo (2 mbar).

This gives the compound of the formula

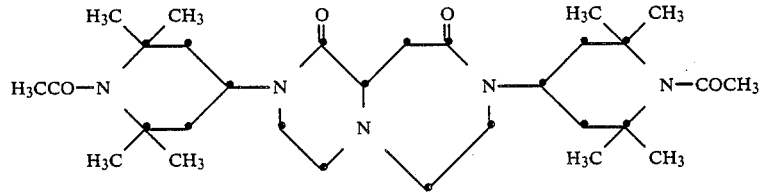

of melting point 282°–284° C.

Analysis for $C_{30}H_{51}N_5O_4$:

Calculated: C=66.02%; H=9.42%; N=12.83%
Found: C—66.12%; H=9.36%; N=12.82%

EXAMPLE 6

1 g of each of the compounds indicated in Table 1, 0.5 g of tris-(2,4-di-t-butylphenyl) phosphite, 0.5 g of pentaerythritol tetrakis[3-(3,5-di-t-butyl-4-hydroxyphenyl)-propionate]and 1 g of calcium stearate are mixed in a slow mixer with 1,000 g of polypropylene powder of melt index =3 g/10 minutes (measured at 230° C. and 2.16 kg). The mixtures are extruded at 200°–220° C. to give polymer granules which are then converted into stretched tapes of 50 μm thickness and 2.5 mm width, using a pilot type apparatus (Leonard Sumirago (VA) Italy) under the following working conditions:

| | |
|---|---|
| extruder temperature = | 210–230° C. |
| head temperature = | 240–260° C. |
| stretch ratio = | 1:6 |

The tapes thus prepared are exposed, mounted on a white card, in a model 65WR Weather-O-meter (ASTM G 26-77), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

Tapes prepared under the same conditions as indicated above, but without the addition of stabilizers, are exposed for comparison.

The results obtained are shown in Table 1.

TABLE 1

| Stabilizer | $T_{50}$ (hours) |
|---|---|
| Without stabilizer | 380 |

TABLE 1-continued

| Stabilizer | $T_{50}$ (hours) |
|---|---|
| Compound of Example 1 | 1920 |
| Compound of Example 2 | 1810 |
| Compound of Example 3 | 1720 |
| Compound of Example 4 | 1700 |

EXAMPLE 7

The stabilizers indicated in Table 2 and 1,000 g of poly(2,6-dimethyl-1,4-phenylene oxide) and high impact polystyrene blend (®Noryl SE 100-960P, General Electric Corp.) are mixed in a slow mixer. The mixture is extruded at 240°–250° C. to give polymer granules which are then converted into 2 mm thick plaques by compression-injection at 270° C. The plaques obtained are exposed in a Xenotest 150 with a black panel temperature of 45° C., up to a yellow index increase of 20 units ($\Delta Y_{20}$).

The results are shown below.

TABLE 2

| Stabilizer | $\Delta Y_{20}$ (hours) |
|---|---|
| None | 240 |
| 3% by weight of the compound of Example 1 + 1% by weight of 2-hydroxy-4-octyloxybenzophenone | 650 |

What is claimed is:

1. A compound of the formula (I)

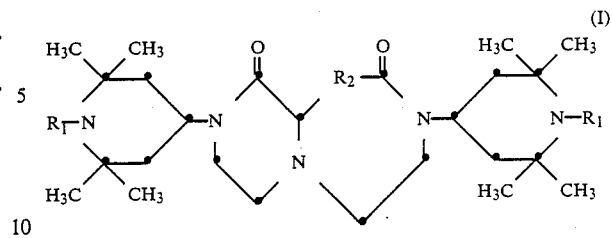

in which $R_1$ is hydrogen, O·, OH, NO, CH$_2$CN, $C_1$–$C_8$-alkyl, allyl, benzyl, $C_1$–$C_8$-acyl, OH-monosubstituted $C_2$–$C_4$-alkyl, 2,3-epoxypropyl, $C_1$–$C_{18}$-alkyloxy, $C_5$–$C_{12}$-cycloalkyloxy or 2,3-dihydroxypropyl and $R_2$ is a direct bond or —CH$_2$—.

2. A compound of the formula (I) according to claim 1, in which $R_1$ is hydrogen, CH$_2$CN, $C_1$–$C_4$-alkyl, allyl, benzyl, acetyl or OH-monosubstituted $C_2$–$C_3$-alkyl.

3. A compound of the formula (I) according to claim 1, in which $R_1$ is hydrogen, methyl, allyl or acetyl.

4. A compound of the formula (I) according to claim 1, in which $R_1$ is hydrogen, methyl, allyl or acetyl and $R_2$ is —CH$_2$—.

5. A compound of the formula (I) according to claim 1, in which $R_1$ is hydrogen or methyl and $R_2$ is —CH$_2$—.

6. A composition comprising an organic material subject to thermal, oxidative or light-induced degradation and an effective stabilizing amount of a compound of the formula (I) according to claim 1.

7. A composition according to claim 6, wherein the organic material is a synthetic polymer.

8. A composition according to claim 7, which, in addition to the compound of the formula (I), also comprises other conventional additives for synthetic polymers.

9. A composition according to claim 6, wherein the organic material is a polyolefine.

10. A composition according to claim 6, wherein the organic material is polyethylene or polypropylene.

11. A composition according to claim 6, wherein the organic material is a poly(phenylene oxide).

12. A method for stabilizing an organic material against thermal, oxidative or light-induced degradation, which comprises incorporating into the organic material an effective stabilizing amount of a compound of the formula (I) according to claim 1.

* * * * *